US011213353B2

(12) United States Patent
Frushour

(10) Patent No.: US 11,213,353 B2
(45) Date of Patent: Jan. 4, 2022

(54) SYSTEMS AND METHODS FOR PLANNING A SURGICAL PROCEDURE AND EVALUATING THE PERFORMANCE OF A SURGICAL PROCEDURE

(71) Applicant: COVIDIEN LP, Mansfield, MA (US)

(72) Inventor: Scott E. M. Frushour, Boulder, CO (US)

(73) Assignee: Covidien LP, Mansfield, MA (US)

( * ) Notice: Subject to any disclaimer, the term of this patent is extended or adjusted under 35 U.S.C. 154(b) by 296 days.

(21) Appl. No.: 15/682,630

(22) Filed: Aug. 22, 2017

(65) Prior Publication Data

US 2019/0059997 A1 Feb. 28, 2019

(51) Int. Cl.
*A61B 34/10* (2016.01)
*G16H 50/70* (2018.01)
(Continued)

(52) U.S. Cl.
CPC .............. *A61B 34/10* (2016.02); *G06Q 50/22* (2013.01); *G09B 23/28* (2013.01); *G16H 10/60* (2018.01);
(Continued)

(58) Field of Classification Search
CPC .............. A61B 34/25; A61B 2034/105; A61B 2034/107; A61B 2034/2051; A61B 34/30;
(Continued)

(56) References Cited

U.S. PATENT DOCUMENTS 8,521,552 B2  8/2013  Niwa
2004/0024288 A1*  2/2004  Uchikubo .......... A61B 1/00045
                                                        600/101
(Continued)

FOREIGN PATENT DOCUMENTS

WO  WO-2014043661 A2 *  3/2014  ........... A61B 5/4509

OTHER PUBLICATIONS

Logan, Heather et al., Exploratory benchtop study evaluating the use of surgical design and simulation in fibula free flap mandibular reconstruction, Journal of Otolaryngology—Head & Neck Surgery, 42(1), 42. (Year: 2013).*

*Primary Examiner* — Hiep V Nguyen
(74) *Attorney, Agent, or Firm* — Carter, DeLuca & Farrell LLP

(57) ABSTRACT

A system facilitating planning of a surgical procedure includes one or more storage devices, one or more input devices, a processor, and a memory. The storage device(s) stores, for previous surgical procedures, surgical instrument information, procedure information, and patient information. The input device(s) is configured to receive procedure information and patient information corresponding to a surgical procedure to be performed. The memory stores instructions that, when executed by the processor, cause the processor to identify similar previous surgical procedures, identify outcome information for each of the similar previous surgical procedures, determine whether there is a correlation between the surgical instrument information of the similar previous surgical procedures and the outcome information of the similar previous surgical procedures, and, if a correlation is determined, output the correlation to facilitate planning of the surgical procedure to be performed.

14 Claims, 4 Drawing Sheets

(51) Int. Cl.
*G06Q 50/22* (2018.01)
*G09B 23/28* (2006.01)
*G16H 10/60* (2018.01)
*G16H 20/40* (2018.01)
*G16H 70/20* (2018.01)

(52) U.S. Cl.
CPC ............. *G16H 20/40* (2018.01); *G16H 50/70* (2018.01); *A61B 2034/101* (2016.02); *G16H 70/20* (2018.01)

(58) Field of Classification Search
CPC ........ A61B 34/70; G16H 40/20; G16H 20/40; G16H 10/60
USPC .............................................................. 705/2
See application file for complete search history.

(56) References Cited

U.S. PATENT DOCUMENTS

| | | | |
|---|---|---|---|
| 2004/0073279 A1* | 4/2004 | Malackowski | A61B 90/36 607/88 |
| 2007/0172803 A1 | 7/2007 | Hannaford et al. | |
| 2008/0140371 A1 | 6/2008 | Warner | |
| 2012/0189996 A1 | 7/2012 | Hager et al. | |
| 2012/0274631 A1* | 11/2012 | Friedland | G06T 19/20 345/419 |
| 2013/0253480 A1 | 9/2013 | Kimball et al. | |
| 2013/0267947 A1* | 10/2013 | Orszulak | A61B 18/1233 606/41 |
| 2013/0296908 A1* | 11/2013 | Schulte | A61B 18/1206 606/169 |
| 2013/0311199 A1 | 11/2013 | Mirlay | |
| 2014/0013565 A1* | 1/2014 | MacDonald | G06F 19/32 29/407.05 |
| 2014/0081659 A1* | 3/2014 | Nawana | G16Z 99/00 705/3 |
| 2014/0148816 A1 | 5/2014 | McDonald et al. | |
| 2014/0171791 A1 | 6/2014 | Simon et al. | |
| 2014/0287393 A1 | 9/2014 | Kumar et al. | |
| 2015/0261922 A1 | 9/2015 | Nawana et al. | |

\* cited by examiner

SYSTEMS AND METHODS FOR PLANNING A SURGICAL PROCEDURE AND EVALUATING THE PERFORMANCE OF A SURGICAL PROCEDURE

BACKGROUND

Technical Field

The present disclosure relates to surgical planning and evaluation and, more particular, to systems and methods facilitating planning of a surgical procedure utilizing data from prior similar surgical procedures and/or evaluating performance of a surgical procedure utilizing data from targeted prior surgical procedures.

Background of Related Art

A particular surgical task may be performed using various different surgical instruments. Even where the same instruments are utilized, the sequence and/or manner in which the instruments are utilized may vary greatly. The selection of different instruments, the use of instruments in different sequences, and/or the use of instruments in different manners may be based on a multitude of factors including patient-based factors (condition, demographics, medical history, genetic/family history information, etc.), environmental factors (geographical location, instrumentation available, patient length of stay, etc.), surgeon-based factors (surgeon's training/education, surgeon's preference, surgeon's experience etc.), and/or pre-surgical evaluation-based factors (pathology reports, surgeon's pre-operative notes, etc.)

Given the larger number of factors involved, determining the instruments, sequence of use of the instruments, and manner of use of the instruments that is likely to yield the best patient outcome is exceedingly difficult. Likewise, evaluating the performance of a surgical procedure is exceedingly difficult given the numerous factors, aside from the performance of the surgeon, that may affect the outcome.

It would therefore be advantageous to provide systems and methods that facilitate planning of a surgical procedure and/or evaluating performance of a surgical procedure.

SUMMARY

As used herein, the term "distal" refers to a portion that is being described which is further from a user, while the term "proximal" refers to a portion that is being described which is closer to a user. Further, to the extent consistent, any of the aspects described herein may be used in conjunction with any or all of the other aspects described herein.

A system facilitating planning of a surgical procedure provided in accordance with the present disclosure includes one or more storage devices, one or more input devices, a processor, and a memory. The storage device(s) stores, for each of a plurality of previous surgical procedures, surgical instrument information, procedure information, and patient information. The input device(s) is configured to receive procedure information and patient information corresponding to a surgical procedure to be performed. The memory stores instructions that, when executed by the processor, cause the processor to identify similar previous surgical procedures by comparing the procedure information and the patient information of the surgical procedure to be performed with the procedure information and the patient information of the plurality of previous surgical procedures, identify outcome information for each of the similar previous surgical procedures, determine whether there is a correlation between the surgical instrument information of the similar previous surgical procedures and the outcome information of the similar previous surgical procedures, and if a correlation is determined, output the correlation to facilitate planning of the surgical procedure to be performed.

In aspects of the present disclosure, the patient information for each of the plurality of previous surgical procedures and/or the patient information for the surgical procedure to be performed include patient demographic information.

In aspects of the present disclosure, the procedure information for each of the plurality of previous surgical procedures and/or the procedure information for the surgical procedure to be performed includes information regarding one or more surgical tasks.

In aspects of the present disclosure, the surgical instrument information for each of the plurality of previous surgical procedures includes surgical instrument type information and surgical instrument activation information.

In aspects of the present disclosure, the system further includes a plurality of surgical instruments configured to record surgical instrument information corresponding thereto during use thereof. The recorded surgical instrument information is transmitted to the storage device(s) for storage as part of the surgical instrument information for each of the plurality of previous surgical procedures.

A method facilitating planning of a surgical procedure provided in accordance with the present disclosure includes storing, for each of a plurality of previous surgical procedures, surgical instrument information, procedure information, and patient information. The method further includes receiving procedure information and patient information corresponding to a surgical procedure to be performed, identifying similar previous surgical procedures by comparing the procedure information and the patient information of the surgical procedure to be performed with the procedure information and the patient information of the plurality of previous surgical procedures, identifying outcome information for each of the similar previous surgical procedures, determining whether there is a correlation between the surgical instrument information of the similar previous surgical procedures and the outcome information of the similar previous surgical procedures, and, if a correlation is determined, outputting the correlation to facilitate planning of the surgical procedure to be performed.

In aspects of the present disclosure, the method initially includes recording the surgical instrument information for each of the plurality of previous surgical procedures during each of the plurality of previous surgical procedures, and transmitting the surgical instrument information for storage thereof.

In aspects of the present disclosure, receiving the procedure information corresponding to the surgical procedure to be performed includes receiving the procedure information from a manual input and/or an EMR. Receiving the patient information corresponding to the surgical procedure to be performed may additionally or alternatively include receiving the procedure information from a manual input and/or an EMR.

In aspects of the present disclosure, the patient information for each of the plurality of previous surgical procedures and/or the patient information for the surgical procedure to be performed include patient demographic information.

In aspects of the present disclosure, the procedure information for each of the plurality of previous surgical procedures and/or the procedure information for the surgical procedure to be performed includes information regarding one or more surgical tasks.

In aspects of the present disclosure, the surgical instrument information for each of the plurality of previous surgical procedures includes surgical instrument type information and surgical instrument activation information.

In aspects of the present disclosure, the method further includes identifying previously determined correlations and, if previously determined correlations are identified, outputting the previously determined correlation to facilitate planning of the surgical procedure to be performed.

A method for evaluating performance of a surgical procedure provided in accordance with the present disclosure includes storing, for each of a plurality of previous surgical procedures: surgical instrument information, procedure information, and patient information. The method further includes receiving surgical instrument information, procedure information, and patient information corresponding to a surgical procedure to be evaluated, identifying target previous surgical procedures based on the procedure information and the patient information of the plurality of previous surgical procedures, comparing the surgical instrument information of the surgical procedure to be evaluated with the surgical instrument information of the target previous surgical procedures, and outputting the comparison to enable evaluation of performance of the surgical procedure to be evaluated.

In aspects of the present disclosure, identifying the target previous surgical procedures includes comparing the procedure information and the patient information of the surgical procedure to be evaluated with the procedure information and the patient information of the plurality of previous surgical procedures. Alternatively or additionally, identifying the target previous surgical procedures may include searching the procedure information and the patient information of the plurality of previous surgical procedures for target information.

In aspects of the present disclosure, the target previous surgical procedures are identified based on the procedure information and the patient information of successful ones of the plurality of previous surgical procedures.

In aspects of the present disclosure, the patient information for each of the plurality of previous surgical procedures and/or the patient information for the surgical procedure to be evaluated includes patient demographic information.

In aspects of the present disclosure, the procedure information for each of the plurality of previous surgical procedures and/or the procedure information for the surgical procedure to be evaluated includes information regarding one or more surgical tasks.

In aspects of the present disclosure, the surgical instrument information for each of the plurality of previous surgical procedures and/or the surgical instrument information for the surgical procedure to be evaluated includes surgical instrument type information and surgical instrument activation information.

BRIEF DESCRIPTION OF THE DRAWINGS

Various aspects and features of the present disclosure are described herein with reference to the drawings wherein.

DETAILED DESCRIPTION

Figure 1:
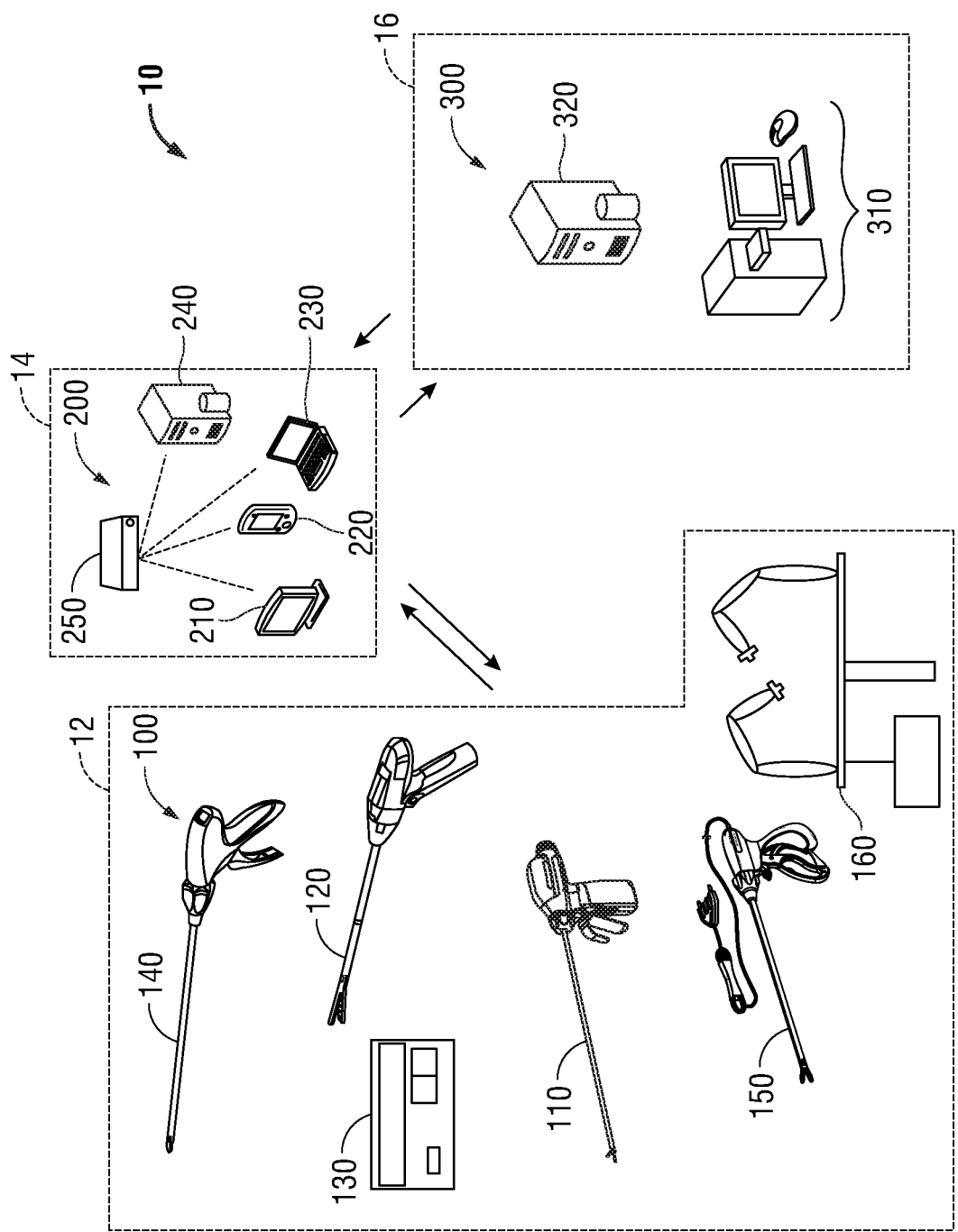
FIG. 1 is a schematic illustration of a system provided in accordance with the present disclosure including a surgical area having one or more surgical instruments, a local area having one or more devices, and a remote area having one or more devices.

Turning to FIG. 1, a system provided in accordance with the present disclosure is shown generally identified by reference numeral 10. System 10 extends over one or more surgical areas 12, one or more local areas 14, and one or more remote areas 16, although other configurations are also contemplated. Each surgical area 12 is an area wherein surgical procedures are performed. As can be appreciated, a plurality of surgical areas 12 across a hospital network, political or geographical area, etc. may be included in system 10. Each surgical area 12 includes a plurality of surgical instruments 100, e.g., a cordless ultrasonic dissector and coagulator 110, a powered surgical stapler 120, an electrosurgical generator 130, a surgical clip applier 140, an electrosurgical forceps 150, and a robotic surgical system 160, some or all of which are configured for use complementarily with one another or alternatively to one another. One or more of surgical instruments 100 may be configured to obtain, store, and/or transmit surgical instrument information such as, for example: identifying information of the surgical instrument(s) 100; a number, pattern, sequence, and/or density of activations (e.g., energy activations, firings, articulations, rotations, etc.) of surgical instrument(s) 100; power level settings of surgical instrument(s) 100; modes of operation of surgical instrument(s) 100; time duration of activations of surgical instrument(s) 100; electrical parameters of surgical instrument(s) 100; pressure, temperature, or other feedback data received from surgical instrument(s) 100 regarding surgical instrument(s) 100 and/or patient tissue; and/or other operational data, usage data, status data, notifications, etc. In addition or as an alternative to surgical instrument(s) 100 obtaining, storing, and/or transmitting the surgical instrument information, such information may be obtained, stored, and/or transmitted with other instrument(s) and/or manually. Further, although particular surgical instruments 110, 120, 130, 140, 150, 160 are illustrated, other suitable surgical instruments may additionally or alternatively be utilized in accordance with the present disclosure. Likewise, different surgical areas 12 may include different surgical instruments 100 or combinations of instruments 100.

Each local area 14 is an area where medical professionals, e.g., surgeons, nurses, technicians, etc., prepare for, perform, and/or follow-up on surgical procedures. Thus, one or more of the local areas 14 may partially or fully overlap, encompass, or be encompassed by one or more of the surgical areas 12. Each local area 14 includes one or more devices 200, e.g., a graphical user interface 210, tablet or smartphone 220, personal computer 230, server 240, and/or router 250. Remote area 16 is an area remote from surgical area(s) 12 where data is received, stored, and/or transmitted. Remote area 16 includes one or more devices 300, e.g., a personal computer 310 and a server 320, although it is contemplated that remote area and one or more of the local areas 14 may be at least partially interchangeable or one and the same (local or remote relative to surgical area(s) 12).

Devices 200, 300 are configured to receive, store, and/or transmit the surgical instrument information, patient information, and procedure information. Patient information may include information regarding a patient that has or will undergo a particular surgical procedure. Such information, more specifically, may include: a patient's condition, demographics (age, height/weight, sex, ethnicity, etc.), medical history, genetic/family history, patient length of stay information, pathology information, patient indications/symptoms, etc. Patient information may be input by a patient, medical professional, or other personnel; may be retrieved from an electronic medical record (EMR); and/or may be extracted from another information database, for example. Suitable security and encryption protocols may be implemented on or across devices 200, 300 and/or other components of system 10 or in communication therewith to ensure HIPAA compliance.

Procedure information includes information regarding a surgical procedure. Such information, more specifically, includes: the surgical task(s) intended to be performed and/or actually performed or attempted, surgical team information (number of team members, number of surgeons, surgeon's training/education, surgeon's preference, surgeon's experience, etc.), hospital geographical data (country, state, zip code), outcome information (whether or not the surgical task(s) was successful, post-surgical recovery information, incremented survival data, complications, unusual findings/results), etc. Procedure information may be input by a patient, medical professional, or other personnel; may be retrieved from an electronic medical record (EMR); and/or may be extracted from another source, e.g., government (CDC, FDA, etc.) database, published study, etc., for example.

Devices 200 and/or devices 300 are configured to associate the surgical instrument information, patient information, and procedure information for each surgical procedure and to store the same in one or more searchable databases. These one or more databases, as detailed below, may be utilized to facilitate planning of a surgical procedure by enabling a user to retrieve information from prior similar surgical procedures and/or to evaluate performance of a surgical procedure utilizing information from targeted prior surgical procedures.

Figure 2:
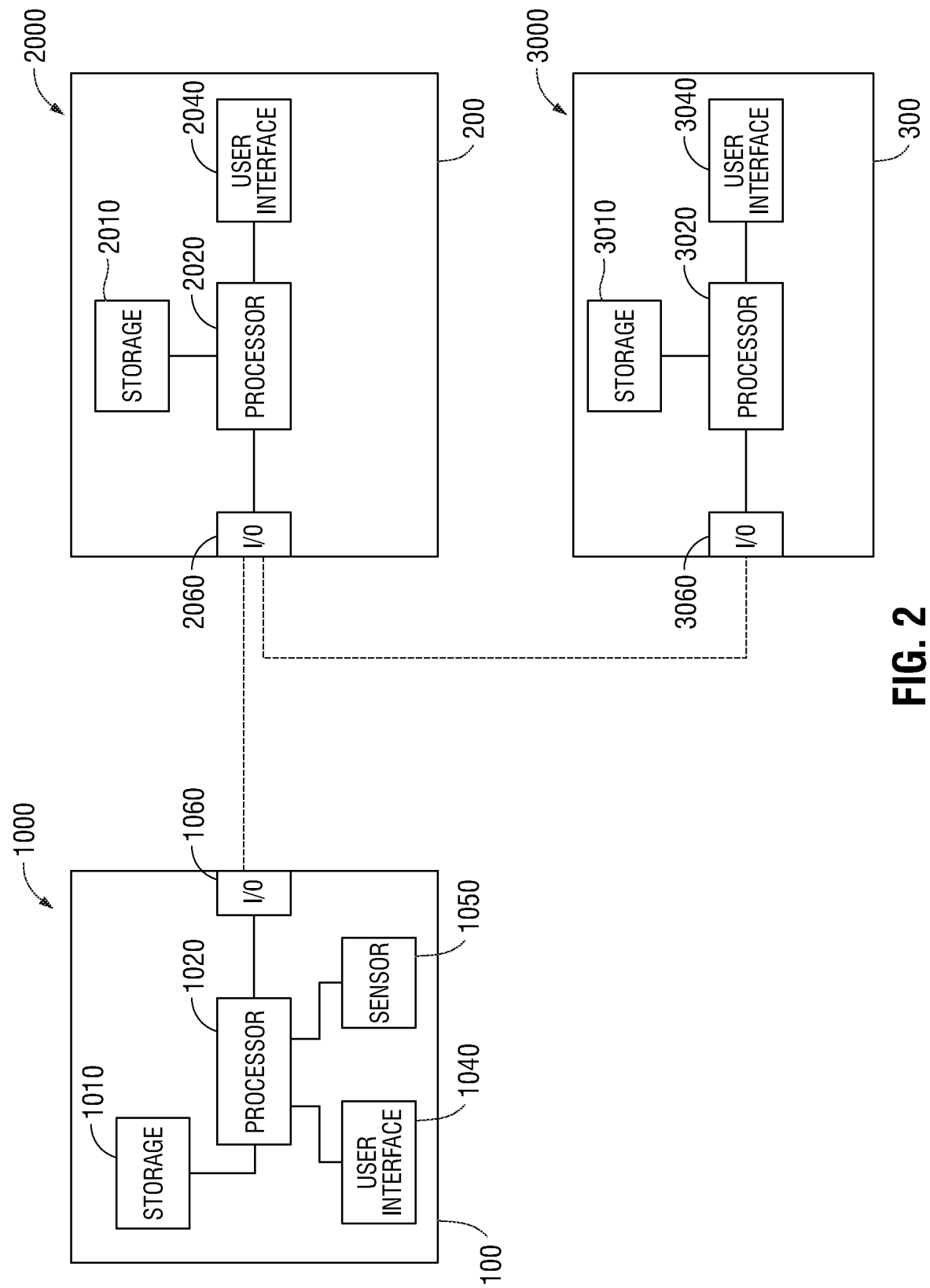
FIG. 2 is a block diagram of one of the surgical instruments of the surgical area, one of the devices of the local area, and one of the devices of the remote area of the system of FIG. 1.

Referring to FIG. 2, in conjunction with FIG. 1, a configuration 1000 of one or more of the surgical instruments 100 of surgical area 12, a configuration 2000 of one or more of the devices 200 of local area 14, and a configuration 3000 of one or more of the devices 300 of remote area 16 are illustrated, although the aspects and features detailed hereinbelow likewise apply to other surgical instruments 100, devices 200, and devices 300. Although only one configuration 1000 is detailed below, it is understood that for each surgical instrument 100 or combination of surgical instruments 100 configured for use with one another, a configuration 1000 is provided. As such, surgical instrument information, as detailed below, may be relayed from each of a plurality of surgical instruments 100 or combination of surgical instruments 100 to devices 200, 300. Likewise, multiple configurations 2000, 3000 may be provided.

Configuration 1000 may be implemented within one surgical instrument 100, e.g., cordless ultrasonic dissector and coagulator 110 or powered surgical stapler 120, or may be implemented across multiple surgical instruments 100, e.g., electrosurgical forceps 1050 and electrosurgical generator 1030. Configuration 1000 includes, for example, a storage device 1010, a processor 1020, a user interface (UI) 1040, one or more sensors 1050, and an input/output 1060. Storage device 1010 may include any suitable component(s), e.g., a magnetic disk, flash memory, optical disk, or other suitable data storage device, operable for storing surgical instrument information obtained during the use of the one or more surgical instruments 100.

Processor 1020 may include any suitable component(s), e.g., a central processing unit (CPU) and a memory, operable to execute instructions to operate the one or more surgical instruments 100 and to receive, process, manipulate, and/or output the information stored in storage device 1010.

User interface (UI) 1040 includes any actuators, buttons, switches, GUI's, etc. of surgical instrument 100 that enable a user to operate the one or more surgical instruments 100. Inputs into UI 1040 may directly operate the one or more surgical instruments 100, e.g., in the case of mechanical component, electromechanical components, or electrical switching components. Alternatively or additionally, inputs into UI 1040 may be fed to processor 1020 to enable processor 1020 to operate the one or more surgical instruments 100 in accordance with the input(s) provided and/or communicate with other devices and/or instruments to effect operation of the one or more surgical instruments 100 in a particular manner. Some or all of the information utilized in operating the one or more surgical instruments 100, as can be appreciated, is stored in storage device 1010 as surgical instrument information. UI 1040 may also allow for the input of data, instructions, settings, etc., which may also constitute surgical instrument information to be stored in storage device 1010.

Sensors 1050 may include distinct sensor components disposed on or separate from the one or more surgical instruments 100 and/or may be incorporated into components of the one or more surgical instruments 100, e.g., processor 1020 and/or UI 1040, in electrical, mechanical, electromechanical, software, hardware, combinations thereof, or other suitable configurations so as to enable the collection of surgical instrument information during use of the one or more surgical instruments 100. Thus, sensors 1050 are capable of sensing some or all of the surgical instrument information noted above. With respect to embodiments where configuration 1000 is implemented across electrosurgical forceps 150 and electrosurgical generator 130, for example, sensors 150 may be configured to sense a number, pattern, sequence, and/or density of energy activations and knife deployment activations, time durations of energy activations and knife deployment activations; electrical parameters of input and output energy transmitted between the electrosurgical forceps 150 and the generator 130, pressure, temperature, impedance, or other feedback data received from tissue treated using electrosurgical forceps 150, etc.

With respect to embodiments where configuration 1000 is implemented in cordless ultrasonic dissector and coagulator 110, as another example, sensors 1050 may be configured to sense a number, pattern, sequence, and/or density of ultrasonic activations, power level settings, e.g., high power or lower power, corresponding to each ultrasonic activation, time durations of ultrasonic activations, electrical parameters of the generator, transducer, and/or battery of ultrasonic dissector and coagulator 110, temperature or other feedback data received from ultrasonic dissector and coagulator 110 regarding ultrasonic dissector and coagulator 110 and/or patient tissue, etc.

With respect to embodiments where configuration 1000 is implemented in powered surgical stapler 120, as yet another example, sensors 1050 may be configured to sense keystroke data regarding the number, pattern, sequence, duration, and/or density of depressions of the clamp button, fire button, right articulate button, left articulate button, rotation buttons, etc. Sensors 1050 may further be configured to sense electrical parameters of the battery and/or motors of powered surgical stapler 120, the particular end effector utilized (e.g., linear stapler, circular stapler, the size, type, number of staples contained within the end effector, etc.), the result of any firing(s), e.g., whether a complete, partial, or failed firing was effected, the result of tissue cutting, the gap and/or pressure exerted on clamped and/or stapled tissue, etc.

Regardless of the particular implementation of configuration 1000, the information obtained by sensors 1050 is stored in storage device 1010 as surgical instrument information. Input/output 1060 is provided to facilitate communication of the surgical instrument information from storage device 1010 to other instruments within surgical area 12 and/or to one or more of the devices 200 within local area 14 (and/or one or more of the devices 300 within remote area 16). Input/output 1060 may be configured for wired or wireless communication and may communicate the surgical instrument information in real-time, periodically, upon occurrence of a particular even (entry into standby mode, connection to a charger or other device, etc.), and/or upon request. Input/output 1060 also enables the input of information to configuration 1000, e.g., software updates.

Continuing with reference to FIG. 2, in conjunction with FIG. 1, configuration 2000 may be implemented within one device 200 of local area 14, may be implemented across multiple devices 200 within local area 14, or may be implemented across multiple areas 12, 14, 16. Configuration 2000 may include, for example, one or more storage devices 2010, a processor 2020, a UI 2040, and an input/output 2060. Storage devices 2010 may include any suitable component(s), e.g., a magnetic disk, flash memory, optical disk, or other suitable data storage device, operable for storing the surgical instrument information obtained from the one or more surgical instruments 100 of surgical area 12, e.g., a magnetic disk, flash memory, optical disk, or other suitable data storage device.

Processor 2020 may include any suitable component(s), e.g., a central processing unit (CPU) and a memory, operable to execute instructions to receive, process, manipulate, store, and/or output information. User interface (UI) 2040 includes any GUI, keyboard, mouse, etc. that enable, for example, the input of patient information and/or procedure information. Input/output 2060 is configured to enable the receipt and/or transmission of patient information and/or procedure information, in addition to receiving the surgical instrument information. Some or all of the surgical instrument information, patient information, and/or procedure information received may be processed, manipulated, and stored in storage devices 2010, e.g., in one or more searchable databases. As detailed below, processor 2020 may be configured to search such database(s) of storage device 2010, 3010 and identify similarities and/or correlations between a surgical procedure that will be performed or has been performed ("a current case") and historical cases ("previous cases") stored in the database(s).

Continuing with reference to FIG. 2, in conjunction with FIG. 1, configuration 3000 may be implemented within one device 300 of remote area 16, may be implemented across multiple devices 300 within remote area 16, or may be implemented across multiple areas 12, 14, 16. Configuration 3000 may include, for example, one or more storage devices 3010, a processor 3020, a UI 3040, and an input/output 3060. Storage devices 3010 may include any suitable component(s), e.g., a magnetic disk, flash memory, optical disk, or other suitable data storage device, operable for storing surgical instrument information, patient information, and/or procedure information and may additionally or alternatively store information that may be transmitted or accessed to facilitate processing of the surgical instrument information, patient information, and/or procedure information. For example, storage devices 3010 may store data from surgical instrument manufacturers regarding the surgical instrument(s) 100 to enable the interpretation of the surgical instrument information, may serve as an EMR repository from which patient information and/or procedure information may be retrieved, may store geographic and/or demographic information regarding surgical areas 12, may store education, training, and/or experience information regarding surgeons and/or surgical teams, etc.

Processor 3020 may include any suitable component(s), e.g., a central processing unit (CPU) and a memory, operable to execute instructions to receive, process, manipulate, store, and/or output information. User interface (UI) 3040 includes any GUI, keyboard, mouse, etc. that enable, for example, the input of patient information and/or procedure information. Input/output 3060 is configured to enable the receipt and/or transmission of surgical instrument information, patient information, procedure information, and/or other information useful in processing the surgical instrument information, patient information, and/or procedure information. Some or all of this information may be processed, manipulated, and stored in storage devices 3010, e.g., in one or more searchable databases. In addition to or as an alternative to processor 2020, processor 3020 may be configured to search such database(s) of storage devices 2010, 3010 and identify similarities and/or correlations between a surgical procedure that will be performed or has been performed (referred to hereinbelow as a "current case") and that of historical cases stored in the database(s) (referred to hereinbelow as "previous cases").

As detailed above, devices 200 and/or devices 300 are configured to process, manipulate, and store the surgical instrument information, patient information, and procedure information for each surgical procedure and to store the same in one or more searchable databases to enable the use of such information in planning of a surgical procedure. An exemplary method of the same is detailed below and may be implemented using the above-detailed system 10 or any other suitable system.

Figure 3:
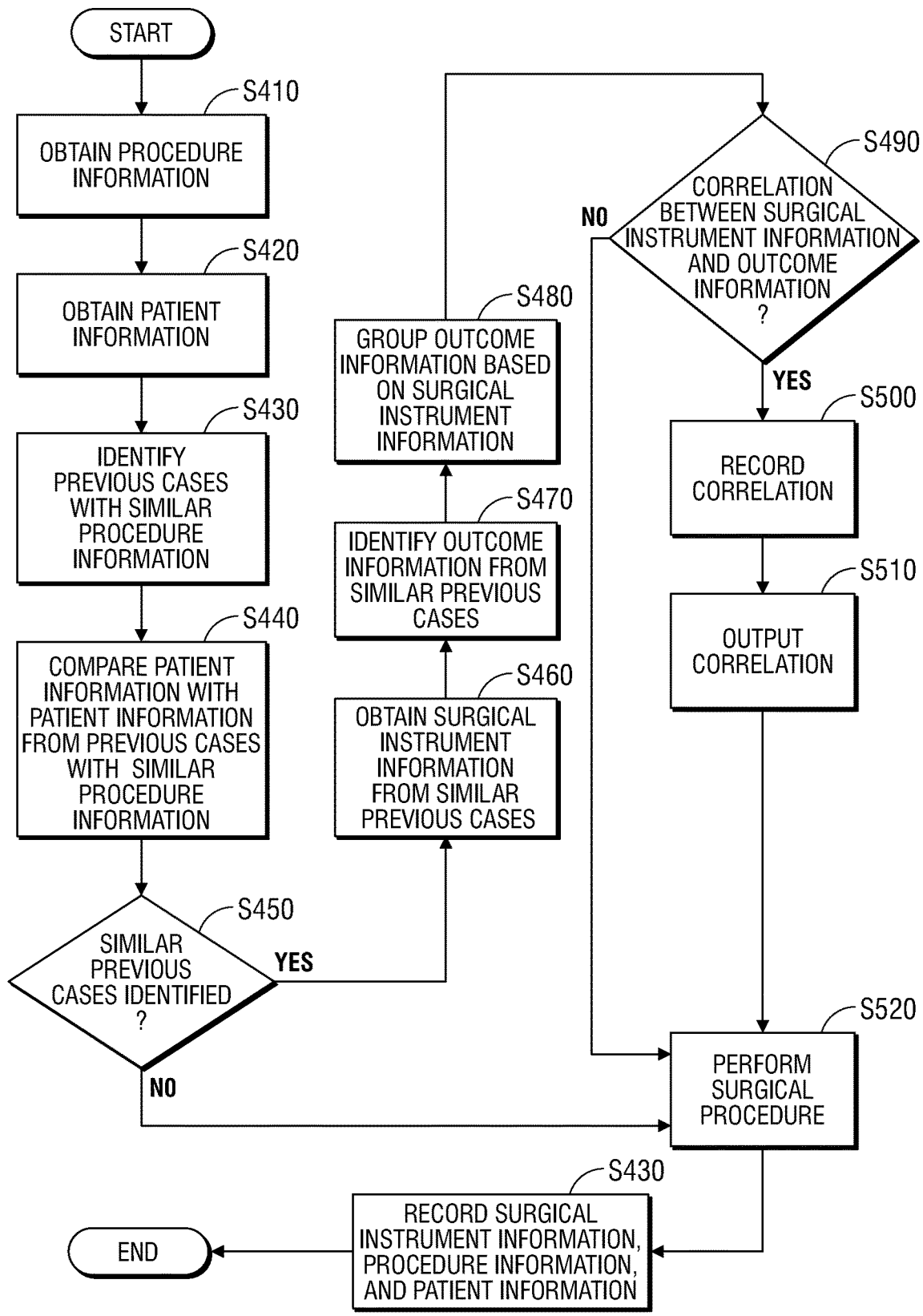
FIG. 3 is a flow diagram illustrating a method of facilitating planning of a surgical procedure provided in accordance with the present disclosure.

Turning to FIG. 3, at S410 and S420, procedure information and patient information, respectively, for a current case are obtained. At S430, previous cases may be searched, e.g., using the searchable database(s) of system 10 (FIG. 1), and the results analyzed, e.g., using processor 2020 and/or processor 3020 (FIG. 2), to identify previous cases with similar procedure information as the current case. Determining whether a previous case includes similar procedure information may be accomplished in any suitable fashion such as, for example, determining a percentage match between the current case procedure information and the procedure information from previous cases. More specifically, with respect to percentage matching, where the percentage of the procedure information from a previous case that matches (within a particular range) the procedure information from the current case meets or exceeds a particular threshold, the procedure information for that previous case is considered to be similar. The percentage matching may be weighted or unweighted, thus enabling the emphasizing or deemphasizing of certain procedure information. Determining whether a previous case includes similar procedure information may also be accomplished by requiring matches of select procedure information. For example, a partial or full match in the surgical task(s) to be performed may result in the procedure information from the previous case being considered similar to that of the current case. Further, percentage matching and matching of select procedure information may be utilized in conjunction with one another, for example, where previous cases with a partial or full match in the surgical task(s) to be performed are first determined and then, from these results, previous cases with similar procedure information are determined based upon a percentage match of other procedure information.

Once previous cases with similar procedure information are identified, the patient information from such cases is compared to the patient information for the current case, as indicated at S440, such that, as indicated at S450, similar previous cases may be identified. Similarly as with the comparison of procedure information, the comparison of patient information may be accomplished using percentage matching, matching of select patient information, or combinations thereof. A "match" with regard to at least some of the patient information may include a match within a particular range. For example, with respect to a current patient that is 57 years old, a match of patient age may be returned for all previous cases where the patent information indicates a patient age from 55 years old to 59 years old. Other patient information, on the other hand, may require a direct match.

Although S410-S440 are detailed wherein determining similar previous cases is accomplished first by comparing procedure information and then comparing those results to patient information, the reverse is also contemplated. That is, similar previous cases may be identified by first comparing patient information and then, utilizing the results thereof, comparing procedure information. Further still, similar previous cases may be determined from a combination of procedure information and patient information concomitantly.

Turning to S450, if an insufficient number of similar previous cases are identified, "NO" at S450, the method proceeds to S520. However, if a sufficient number of similar previous cases are identified, "YES" at S450, the method proceeds to S460, where surgical instrument information from such similar previous cases is obtained. After, prior to, or at the same time as obtaining the surgical instrument information from similar previous cases, outcome information from such similar previous cases is identified, as indicated at S470. The outcome information may be directly pulled from the procedure information, may be separate therefrom, or may be determined based upon the procedure information and/or patient information obtained. Outcome information may include and/or be based on, for example, post-surgical recovery information, incremented survival data (2 weeks, 6 months, 1 year, 5 years, etc.), the extent of success of the surgical task(s) sought to be accomplished, complications, etc.

At S480, the outcome information from the similar previous cases is grouped based upon the surgical instrument information from the similar previous cases such that, as indicated in S490, it can be determined whether there is a correlation between the outcome information and the surgical instrument information for the similar previous cases. Correlations may be determined in any suitable fashion and may indicate direct correlations, e.g., that using a particular set of surgical instruments in a particular manner yields a particular success rate for a given surgical task, or relative correlations, e.g., that using a particular set of surgical instruments in a particular manner is relatively more successful (by a particular percentage) than using another set of surgical instruments and/or the same surgical instruments in a different manner. Further, correlations may include broader correlations, e.g., pertaining to surgical instrument(s) type, and/or more specific correlations, e.g., pertaining to a particular use of the surgical instrument(s).

If no correlation is determined at S490, the method proceeds to S520. However, if a correlation is determined in S490, the correlation is recorded at S500, for future use, and is output at S510. Recording correlations for future use may obviate S460-S480 and enable prior correlations to be identified in S490 in place thereof, or may be used in conjunction with S460-S480 to enable updating of prior correlations with additional data from previous similar cases. The correlation may be output in S510, e.g., displayed on one or more of devices 200, 300 (FIGS. 1 and 2). For example, a table, chart, and/or other graphical display may be provided indicating the correlations determined.

Correlating surgical instrument information and outcome information from prior similar cases and presenting the same facilitates the determination of what surgical instrument(s) to utilize and in what manner to utilize them while minimizing outcome-effecting factors unrelated (or less related) to the surgical instruments(s) utilized and/or the manner in which they are utilized. For example, the above-detailed system 10 (FIG. 1) and method may indicate that, for a particular patient in a particular environment, using a first surgical instrument may provide a greater likelihood of success than using a second surgical instrument, despite overall statistics (across all demographics and environments) indicating that the second surgical instrument provides a greater likelihood of success. As another example, the above-detailed system 10 (FIG. 1) and method may indicate that, despite a particular surgical instrument being generally successful in accomplishing a particular surgical task, over-utilizing the surgical instrument, under-utilizing the surgical instrument, and/or utilizing the surgical instrument in a particular manner may detrimentally impact the likelihood of success of the surgical task.

After using the output correlation information from S510 to determine the appropriate surgical instrument(s) to be utilized and/or the manner of use thereof, the surgical procedure is performed at S520 and the surgical instrument information, patient information, and procedure information is recorded at S530, although at least some of the surgical instrument information, patient information, and procedure information may be obtained and recorded prior to or during the surgical procedure.

The above-detailed system 10 (FIG. 1) and method are further advantageous in that, as more surgical procedures are performed and, thus, more surgical instrument information, procedure information, and patient information is obtained, e.g., as the above-detailed method is repeated, additional and/or more specific correlations may be drawn out, thus further facilitating the planning of future surgical procedures.

Figure 4:
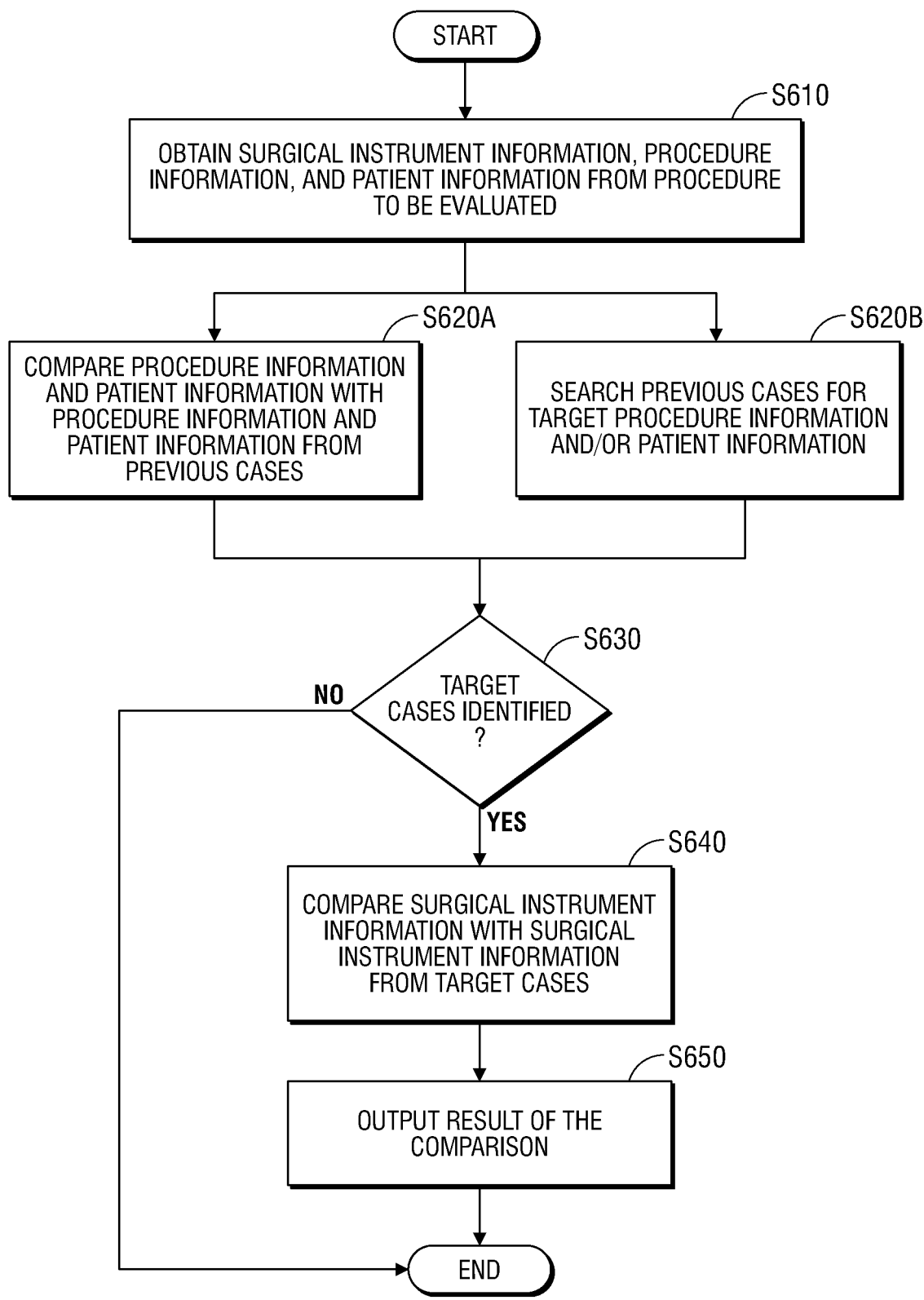
FIG. 4 is a flow diagram illustrating a method of evaluating performance of a surgical procedure provided in accordance with the present disclosure.

Turning to FIG. 4, as detailed above, devices 200 and/or devices 300 (FIGS. 1 and 2) are configured to process, manipulate, and store the surgical instrument information, patient information, and procedure information for each surgical procedure and to store the same in one or more searchable databases to enable the use of such information in evaluating performance of a surgical procedure. A method of the same is detailed below and may be implemented using the above-detailed system 10 (FIG. 1) or any other suitable system.

At S610, surgical instrument information, procedure information, and patient information from the procedure being evaluated are obtained. At S620A, the procedure information and patient information are compared to the procedure information and patient information of previous cases, similarly as detailed above, to identify similar cases. Additionally or alternatively, at S620B, previous cases having particular procedure information and/or patient information are searched to identify particular cases (regardless of whether similar to the procedure being evaluated). Thus, based on S620A and/or S620B, target cases can be identified at S630 from the similar cases, the particular cases, or combinations thereof. More specifically, target cases can be identified by determining previous cases that include: similar procedure information and/or patient information as that of the procedure to be evaluated (e.g., in S620A); and/or selected procedure information and/or patient information (e.g., in S620B). For example, target cases can be identified that are performed by surgeons in other areas and/or with other experience, specialties, support, etc., as identified in S620B, and that are otherwise similar in terms of patient information and/or procedure information, as identified in S620A. As another example, target cases that are similar in terms of patient information and/or procedure information, as identified in S620A, and that have a particular outcome, e.g., success, required post-operative hospital stay, complications, etc., different from the outcome in the procedure being evaluated, as identified in S620B, can be selected.

Turning to S630, if an insufficient number of similar previous cases are identified, "NO" at S630, there is insufficient information to perform an evaluation and the method ends. However, if a sufficient number of similar previous cases are identified, "YES" at S630, the method proceeds to S640, where the surgical instrument information from the target cases is compared to the surgical instrument information from the procedure being evaluated. The results of this comparison are output at S650, e.g., in a table, chart, and/or other graphical display. The output may be displayed, for example, on one or more of devices 200, 300 (FIGS. 1 and 2). Such output may provide a display including, for example, a graph indicating the activation amounts or levels, activation durations, and/or activation sequences of the surgical instruments utilized in the procedure being evaluated versus that of the target case(s) (individually or as an average). As such, it can be determined whether the procedure being evaluated is being performed in a similar manner as the target cases or differently therefrom. If different, such may indicate whether or not the manner in which the procedure was performed impacted the outcome. If similar, such may indicate a technique or other flaw in performance that resulted in a different outcome (if indeed different) despite the procedure being performed in a similar manner. Regardless of the particular display and/or conclusions drawable therefrom, by identifying target cases as detailed above, other variables that my affect the manner in which the procedure was performed and/or the outcome thereof can be minimized and, thus, an evaluation focused on performance of the surgical procedure may be more easily undertaken.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method facilitating planning of a surgical procedure, the method comprising:
   detecting energy activations, for each of a plurality of surgical instruments, as surgical instrument information;
   measuring the time duration for energy activations, for each of the plurality of surgical instruments, as surgical instrument information;
   detecting feedback data received from patient tissue treated with the plurality of surgical instruments, as surgical instrument information;
   transmitting the surgical instrument information, procedure information, and patient information to a plurality of networked devices, wherein the plurality of networked devices are distributed locally, remotely, or across a combination of local and remote sites, wherein the plurality of networked devices collectively function as a processor, the processor:
      storing a record, for each of the plurality of previous surgical procedures, the record including: the surgical instrument information, procedure information, and patient information;
      receiving procedure information and patient information corresponding to a current surgical procedure;
      identifying similar previous surgical procedures by determining a percentage match between the procedure information and the patient information of the current surgical procedure and the procedure information and the patient information of the stored records,
         wherein determining the percentage match includes weighing selected categories of at least one of procedure information or patient information for emphasis,
         wherein, if the percentage match falls within a threshold range, the method further includes:
      identifying outcome information for each of the similar stored records;
      determining whether there is a correlation between the surgical instrument information of the similar stored records and the outcome information of the similar stored records; and
   if a correlation is determined, outputting the correlation to facilitate planning of the current surgical procedure.

2. The method according to claim 1, wherein receiving the procedure information corresponding to the current surgical procedure includes receiving the procedure information from at least one of a manual input or an EMR.

3. The method according to claim 1, wherein receiving the patient information corresponding to the current surgical procedure includes receiving the procedure information from at least one of a manual input or an EMR.

4. The method according to claim 1, wherein the patient information for each stored record and the patient information for the current surgical procedure each includes patient demographic information.

5. The method according to claim 1, wherein the procedure information for each stored record and the procedure information for the current surgical procedure each includes information regarding at least one surgical task.

6. The method according to claim 1, wherein the surgical instrument information for each stored record includes surgical instrument type information.

7. The method according to claim 1, further comprising:
identifying previously determined correlations; and
if previously determined correlations are identified, outputting the previously determined correlation to facilitate planning of the surgical procedure to be performed.

8. A method for evaluating performance of a surgical procedure, the method comprising:
detecting energy activations, for each of a plurality of surgical instruments, as surgical instrument information;
measuring the time duration for energy activations, for each of the plurality of surgical instruments, as surgical instrument information;
detecting feedback data received from patient tissue treated with the plurality of surgical instruments as surgical instrument information;
transmitting the surgical instrument information, procedure information, and patient information to a plurality of networked devices, wherein the plurality of networked devices are distributed locally, remotely, or across a combination of local and remote sites, wherein the plurality of networked devices collectively function as a processor, the processor:
storing a record, for each of the plurality of previous surgical procedures, the record including: the surgical instrument information, procedure information, and patient information;
receiving surgical instrument information, procedure information, and patient information corresponding to a current surgical procedure;
identifying target previous surgical procedures based on the procedure information and the patient information of the stored records;
determining a percentage match between the surgical instrument information of the current surgical procedure to be evaluated and the surgical instrument information of the stored records,
wherein determining the percentage match includes weighing selected categories of at least one of procedure information or patient information for emphasis,
wherein, if the percentage match falls within a threshold range, the method further includes:
outputting the comparison to enable evaluation of performance of the current surgical procedure.

9. The method according to claim 8, wherein identifying the target previous surgical procedures includes comparing the procedure information and the patient information of the current surgical procedure with the procedure information and the patient information of the stored records.

10. The method according to claim 8, wherein identifying the target previous surgical procedures includes searching the procedure information and the patient information of the stored records.

11. The method according to claim 8, wherein the target previous surgical procedures are identified based on the procedure information and the patient information from the stored records of successful surgical procedures.

12. The method according to claim 8, wherein the patient information for each stored record and the patient information for the current surgical procedure each includes patient demographic information.

13. The method according to claim 8, wherein the procedure information for each stored record and the procedure information for the current surgical procedure each includes information regarding at least one surgical task.

14. The method according to claim 8, wherein the surgical instrument information for each stored record and the surgical instrument information for the current surgical procedure each includes surgical instrument type information.

* * * * *